US008430681B2

(12) United States Patent
Wang et al.

(10) Patent No.: US 8,430,681 B2
(45) Date of Patent: Apr. 30, 2013

(54) MULTI-FUNCTION CLIP TO ENGAGE DIFFERENT TYPES OF ELECTRICAL LEADS

(75) Inventors: Gonghua Wang, Nanshan Shenzhen (CN); Gang Liu, Nanshan Shenzhen (CN); Xicheng Xie, Nanshan Shenzhen (CN)

(73) Assignee: Edan Instruments, Inc. (CN)

( * ) Notice: Subject to any disclaimer, the term of this patent is extended or adjusted under 35 U.S.C. 154(b) by 0 days.

(21) Appl. No.: 13/057,139

(22) PCT Filed: Feb. 4, 2010

(86) PCT No.: PCT/CN2010/070514
§ 371 (c)(1),
(2), (4) Date: Feb. 1, 2011

(87) PCT Pub. No.: WO2011/088625
PCT Pub. Date: Jul. 28, 2011

(65) Prior Publication Data
US 2012/0272489 A1    Nov. 1, 2012

(51) Int. Cl.
*H01R 27/00* (2006.01)
(52) U.S. Cl.
USPC .......................................................... 439/217
(58) Field of Classification Search .................. 439/217, 439/437, 105, 108, 219, 506
See application file for complete search history.

(56) References Cited

U.S. PATENT DOCUMENTS

| 2,491,552 | A | * | 12/1949 | De Grace | 439/506 |
| 3,506,944 | A | * | 4/1970 | Potruch | 439/437 |
| 3,641,473 | A | * | 2/1972 | Attaway | 439/108 |
| 4,057,313 | A | * | 11/1977 | Polizzano | 439/219 |
| 4,640,563 | A | * | 2/1987 | LeBlanc | 439/217 |
| 2009/0062636 | A1 | | 3/2009 | Muz | |

FOREIGN PATENT DOCUMENTS

| CN | 85202339 U | 4/1986 |
| CN | 85202644 U | 7/1987 |
| CN | 2845719 Y | 12/2006 |
| CN | 201167950 Y | 12/2008 |
| DE | 19643988 C1 | 4/1998 |

OTHER PUBLICATIONS

International Search Report for PCT application PCT/CN2010/070514; and English translation.
Written Opinion of International Searching Authority for PCT application PCT/CN2010/070514; Dated Sep. 29, 2010; and English translation.

\* cited by examiner

*Primary Examiner* — Chandrika Prasad
(74) *Attorney, Agent, or Firm* — Garcia-Zamor IP Law; Ruy M. Garcia-Zamor

(57) ABSTRACT

A multi-function clamp for veterinarian, mainly includes upper clip and lower clip; the clamp body is composed by upper clip, lower clip, bolt and torsional spring, wherein the foresaid clamp body installed with connection assembly that has connecting lead wires, and the connection assembly has several installation sections coordinates with the lead wire plug. By adopting the compatibility design, the multi-function clamp for veterinarian could apply to wider areas, a pet clinic equipped with the multi-function clamp for veterinarian is applicable even using the probe-type lead wires, the banana plug lead wires, the snap-type lead wires and the clip-type lead wires simultaneously, which greatly decreases the procurement cost for equipment and accessories, and easier to be operated. Furthermore, by adopting the anti-slip design, the multi-function clamp for veterinarian will improve remarkably for the matter the clamp drops off from the operators or the animal skins, which saves time in operation.

11 Claims, 5 Drawing Sheets

MULTI-FUNCTION CLIP TO ENGAGE DIFFERENT TYPES OF ELECTRICAL LEADS

CROSS REFERENCE TO RELATED APPLICATION

The application claims priority to the following patent applications: (1) Patent Cooperation Treaty Application PCT/CN2010/070514 filed Feb. 2, 2010 and (2) Chinese Patent Application No. CN201010101570.1, filed on Jan. 22, 2010; each of the above-identified applications is hereby incorporated by reference herein as if set forth in its entirety.

TECHNICAL FIELD

The invention relates to a multi-function clamp, especially to a clamp for veterinarian that is compatible with many kinds of lead wires and applied to the equipment such as veterinary electrocardiograph, veterinary monitor and so on.

BACKGROUND ART

Clamp for veterinarian currently mainly used in electrocardiograph, veterinary monitors and other products, which clipped in the animal's skin to detect the animal life signs. Currently most of the domestic market is veterinary clamp with a snap (specifically speaking, the connection of the lead wires and the clamp is snap), for which the connection way is relatively unitary; when a pet requires to use the probe-type lead wires or the banana plug lead wires or again use the snap-type lead wires or the clip-type lead wires, the satisfaction could not be fulfilled.

CONTENTS OF THE INVENTION

Aiming at the shortcomings above in existing technology, the invention is to provide a multi-function clamp for veterinarian which is compatible with many kinds of lead wires, decreases the procurement cost for the accessories, increasing the efficiency in usage of the clamp for veterinarian and greatly facilitates the operation.

A multi-function clamp for veterinarian which mainly includes upper clip and lower clip; the clamp body is composed by upper clip, lower clip, bolt and torsional spring, wherein the foresaid clamp body installed with connection assembly that has connecting lead wires, and the connection assembly has several installation sections coordinates with the lead wire plugs.

The foresaid connection assembly includes dual-bore copper and chamfer head screw; the chamfer head screw passes through the lower clip to install with the dual-bore copper, so as to install the dual-bore copper in the foresaid lower clip.

The bottom of the foresaid dual-bore copper is a snap, wherein both sides of the dual-bore copper has mounting holes having a diameter of 3 mm and 4 mm respectively, while the two mounting holes are perpendicular to one another in the axial direction of the hole.

The foresaid connection assembly includes chamfer head screw, single-hole copper and hand screw, wherein the chamfer head screw passes through the lower clip to install with the single-hole copper, so as to lock the single-hole in the lower clip.

The in the side face of the foresaid single-hole copper has a mounting hole having a diameter of 4 mm, wherein the mounting hole installs with the lead wires plug and the hand screw is screwed into the single-hole copper, while screw the hand screw tightly will fix the lead wires plug that inserted in the mounting hole with a diameter of 4 mm.

The bottom of the foresaid hand screw is a snap.

The foresaid connection assembly includes double-headed electrode socket and rivet, wherein by coordination of the rivet and the double-headed electrode socket, so as to install the double-headed electrode socket in the foresaid lower clip.

Both flanks of the foresaid double-headed electrode socket have mounting holes having a diameter of 3 mm and 4 mm respectively, while the bottom of the rivet is a snap.

The foresaid lower clip has tooth, and the connection assembly installs in the foot section of the lower clip.

The tail end of the foresaid lower clip has wavy stripes while the front end has multiple dots, and the upper clip has assorted tooth in the place corresponding to the tooth of the lower clip.

By adopting the compatibility design, the multi-function clamp for veterinarian could apply to wider areas, a pet clinic equipped with the multi-function clamp for veterinarian is applicable even using the probe-type lead wires, the banana plug lead wires, the lead wires with snap and the clip-type lead wires simultaneously, which greatly decreases the procurement cost for equipment and the accessories, and easier to be operated. Furthermore, by adopting the anti-slip design, the multi-function clamp for veterinarian will improve remarkably for the matter the clamp drops off from the operators or the animal skins, which saves time in operation.

MODE OF CARRYING OUT THE INVENTION

Further explanation to the invention is stated below by three embodiment of implementation combining with the attached figures:

Embodiment 1

Figure 1:
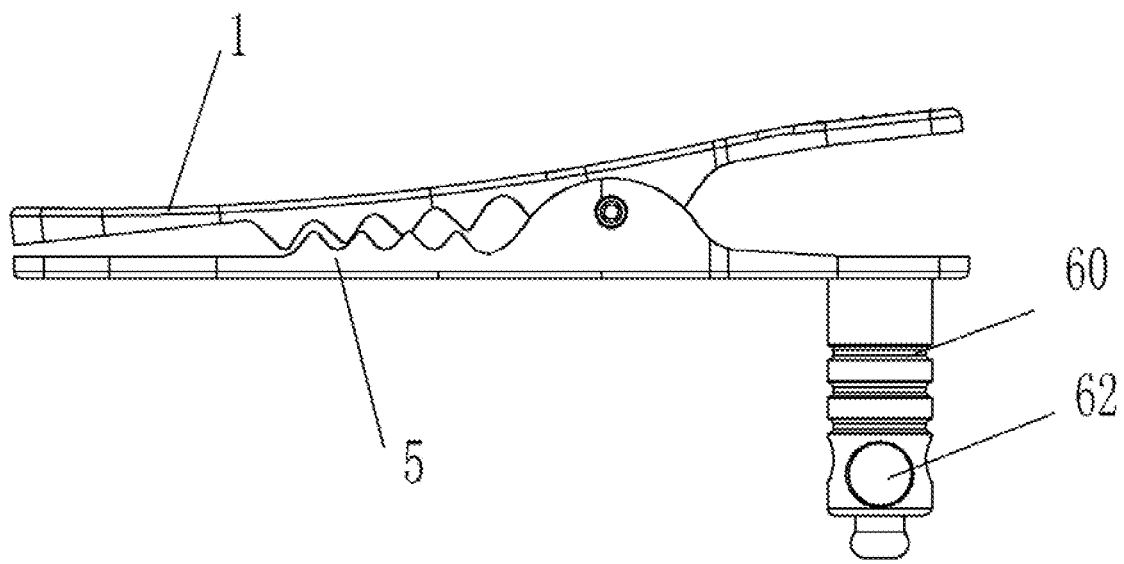
FIG. 1 is the whole structure drawing of embodiment 1 of the invention.
Figure 2:
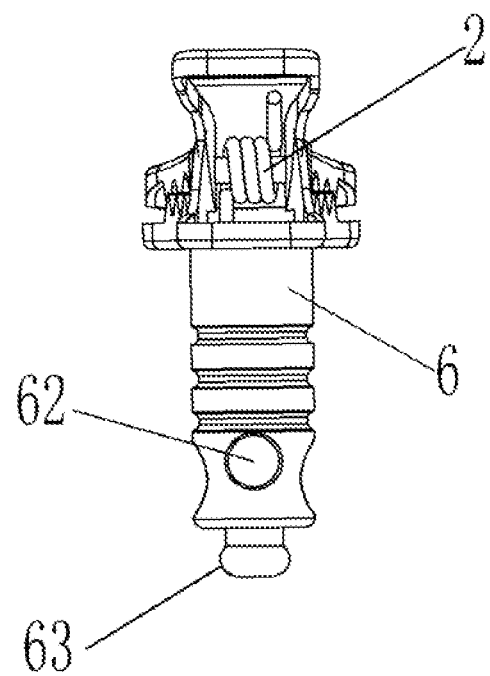
FIG. 2 is the assembly diagram of the connection assembly and the clamp of FIG. 1.
Figure 3:
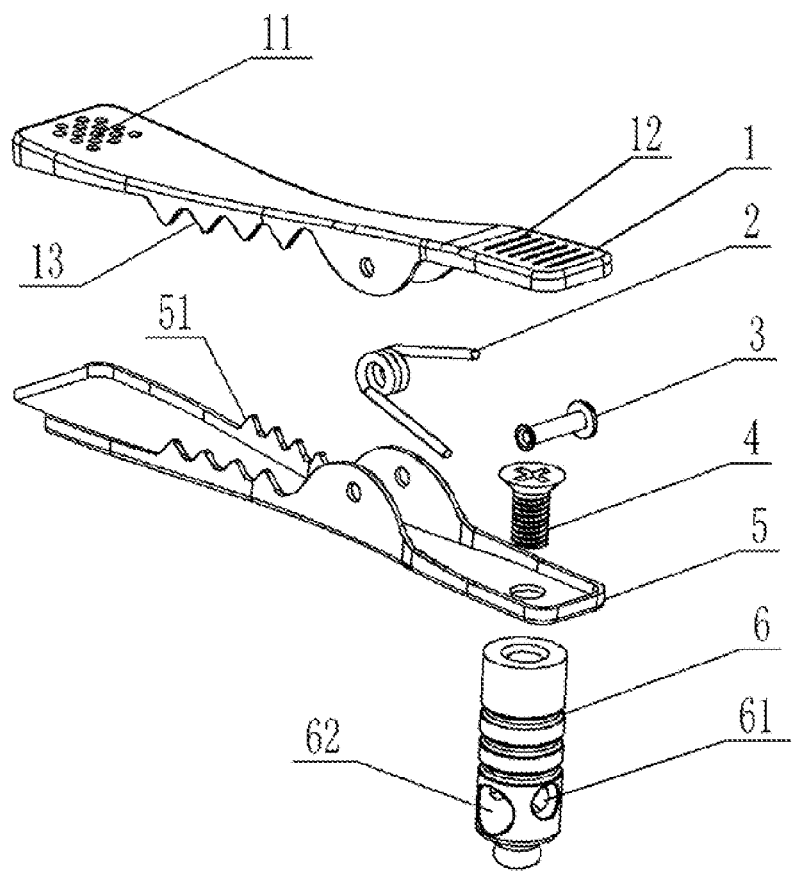
Figure 4:
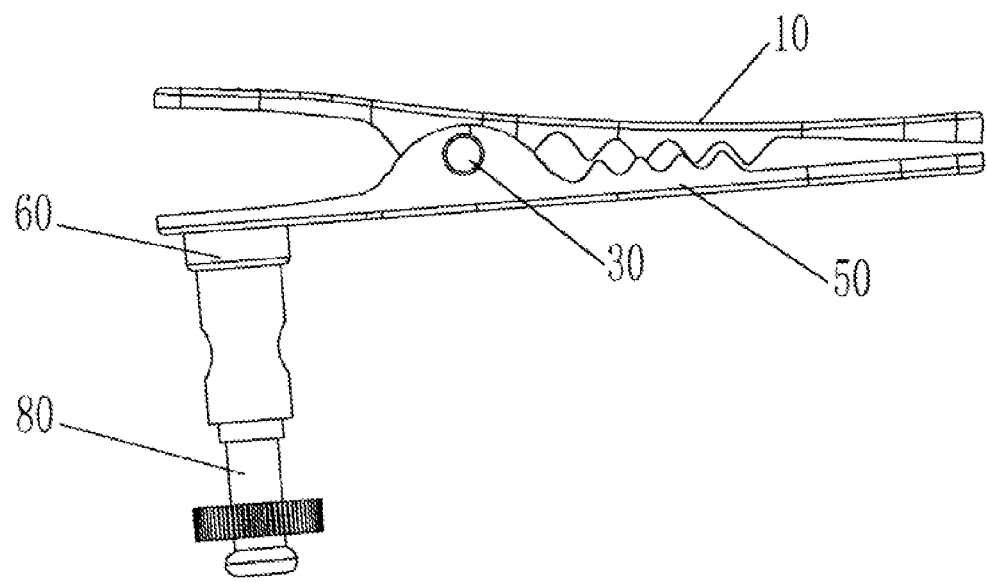
FIG. 4 is the whole structure drawing of embodiment 2 of the invention.
Figure 5:
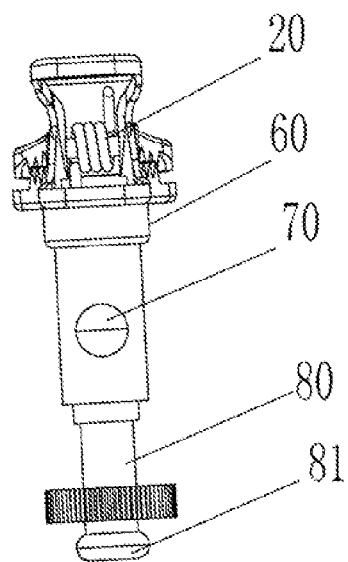
FIG. 5 is the assembly diagram of the connection assembly and the clamp of FIG. 4.
Figure 6:
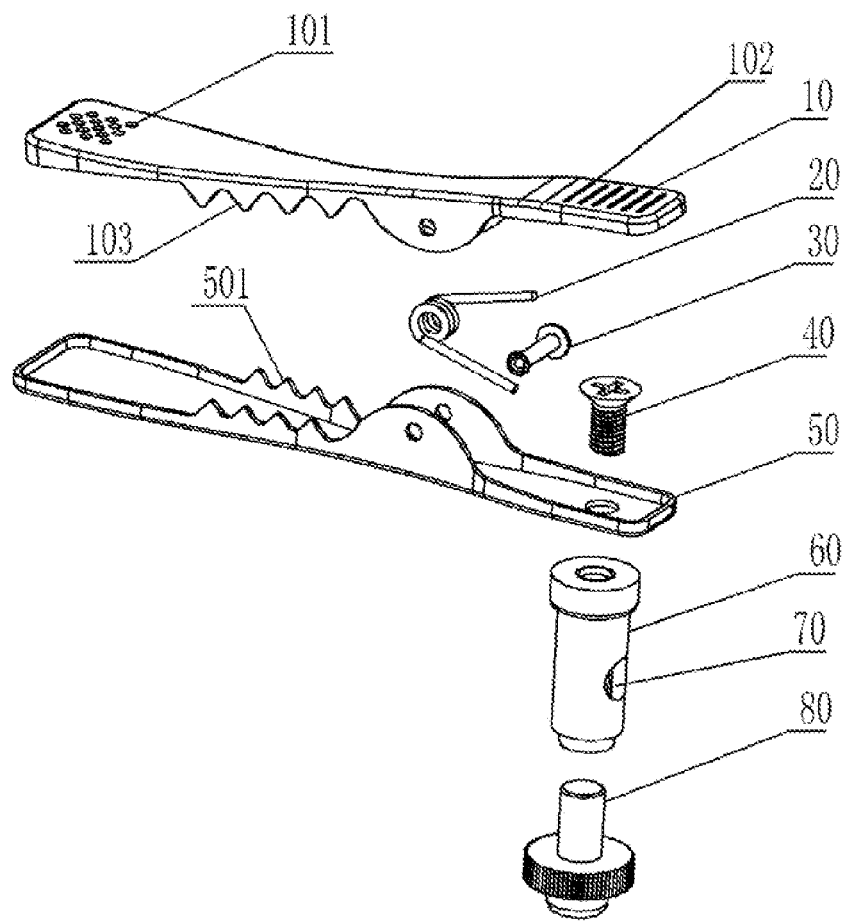
FIG. 6 is the exploded view of the embodiment 2.

The multi-function clamp for veterinarian as shown in FIG. 1, FIG. 2 and FIG. 3 is comprised by upper clip 1, lower clip 5, bolt 3, torsional spring 2 and the connection assembly, where, the connection assembly includes a dual-bore copper 6 wherein the dual-bore copper 6 has two mounting holes and one M3*6 chamfer head screw 4; when assembling, put the lower clip 5 in a plane surface, install the M3*6 chamfer head screw 4 with the dual-bore copper 6 by passing through the lower clip 5, then lock the dual-bore copper 6 in the lower clip 5, at the time the torsional spring 2 is placed in the lower clip 5, cover the upper clip 1 and put on the bolt 3, then press-riveting the upper clip 1 and the lower clip 5 to form an integral clamp for veterinarian. Thereinto, the tail end of the upper clip 1 has wavy stripes 12, for which the main purpose of the stripes is to prevent the clamp drop from the users; the front end of the upper clip 1 has multiple circular dots 11, and between the upper clip 1 and the lower clip 5 has tooth 13 and tooth 51 in separately to prevent the clamp loosing from the animal skins.

The embodiment applies to different types of lead wires, the dual-bore copper 6 has mounting holes 61 with a diameter of 3 mm and mounting holes 62 with a diameter of 4 mm, and at the bottom of the dual-bore copper 6 has snap plug 63 with a diameter of 4 mm; when the user using the electrocardiogram (hereinafter refers as "ECG") cable, if it is a probe-type with a diameter of 3 mm, insert the lead wires into the mounting holes 61 with a diameter of 3 mm for normal usage; if the ECG cable is banana plug type with a diameter of 4 mm, insert the lead wires into the mounting holes 62 with a diameter of 4 mm for normal usage; if f the ECG cable is snap-type with a diameter of 4 mm, insert the lead wires into the snap plug 63 with a diameter of 4 mm for normal usage.

Embodiment 2

Figure 7:
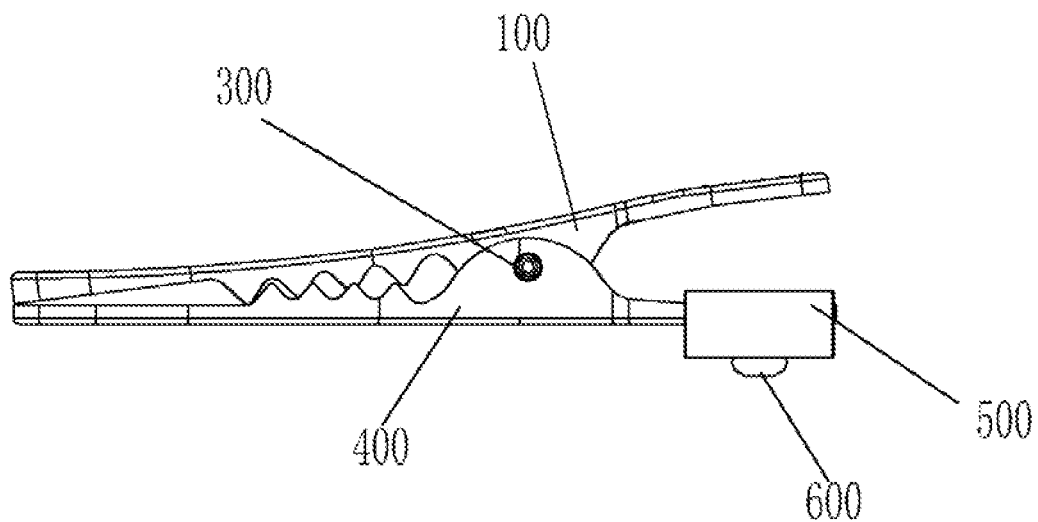
FIG. 7 is the whole structure drawing of embodiment 3 of the invention.
Figure 8:
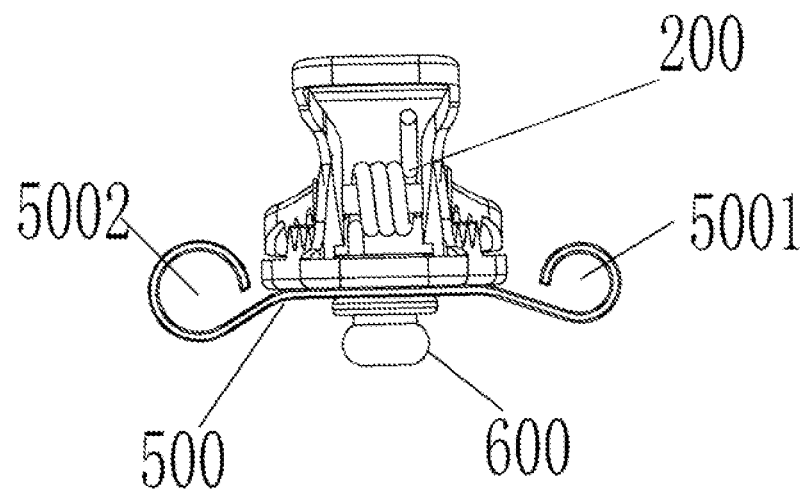
FIG. 8 is the assembly diagram of the connection assembly and the clamp of FIG. 7.
Figure 9:
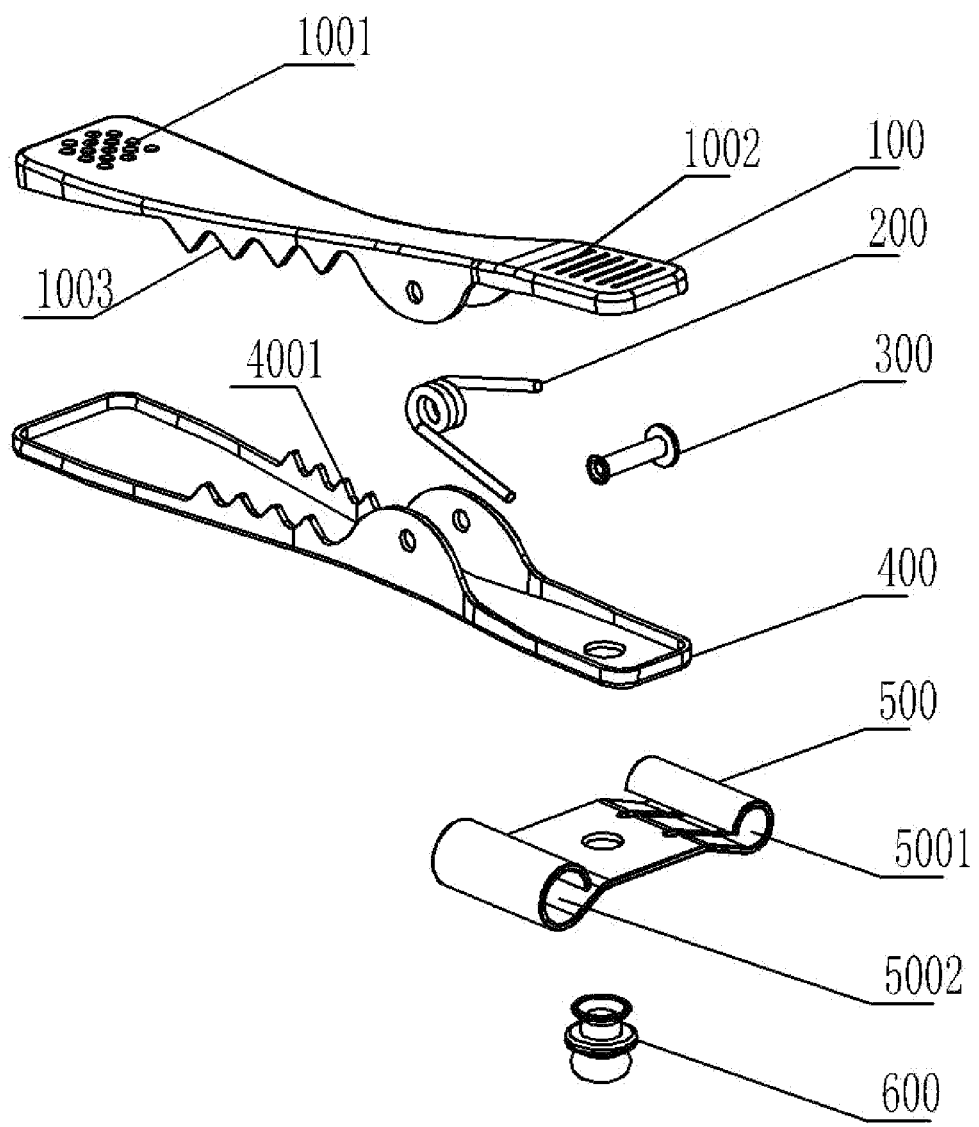
FIG. 9 is the exploded view of the embodiment 3.

The multi-function clamp for veterinarian as shown in FIG. 7, FIG. 8 and FIG. 9 is comprised by upper clip 100, lower clip 400, bolt 300, torsional spring 200 and the connection assembly, where, the connection assembly includes a double-headed electrode socket 500 and rivet 600, wherein the bottom of the rivet 600 has a snap plug; when assembling the clamp for veterinarian, lay flat the lower clip 400, using the rivet 600 to press-rivet the double-headed electrode socket 500 in the lower clip 400, and put the torsional spring 200 in the lower clip 400, then cover the upper clip 100, pass through the bolt 300, and then press-rivet the upper clip 100 and the lower clip 400. Thereinto, the tail end of the upper clip 100 has wavy stripes 1002, for which the main purpose of the stripes is to prevent the clamp drop from the users; the front end of the upper clip 100 has multiple circular dots 1001, and between the upper clip 100 and the lower clip 400 has tooth 1003 and tooth 4001 in separately to prevent the clamp loosing from the animal skins The double-headed electrode socket 500 of the embodiment has probe holes 5001 with a diameter of 3 mm and probe holes 5002 with a diameter of 4 mm, and at the bottom of the snap-rivet 600 has snap plug 63 with a diameter of 4 mm; when the user using the ECG cable, if it is a probe- type with a diameter of 3 mm, insert the lead wires into the probe holes 5001 for normal usage; if the ECG cable has a diameter of (φ is used as a symbol for diameter) φ4 mm banana plug type, insert the lead wires into the probe holes 5002 with a diameter of 4 mm for normal usage; if the ECG cable is snap-type with a diameter of 4 mm, insert the lead wires into the snap plug with a diameter of 4 mm for normal usage.

What is claimed is:

1. A multi-function clamp for veterinarians, comprising: a clamp body having an upper clip and a lower clip; a torsional spring is disposed between the upper clip and the lower clip and secured to the lower clip by a bolt, wherein the clamp body includes a connection assembly that has at least two installation parts configured to engage different types of lead wire plugs.

2. The multi-function clamp of claim 1, wherein the connection assembly includes a dual-bore copper connector and a chamfer head screw; the chamfer head screw positioned through the lower clip to install with the dual-bore copper connector so as to install the dual-bore copper connector in the lower clip.

3. The multi-function clamp of claim 2, wherein the bottom of the dual-bore copper connector forms a snap, wherein both sides of the dual-bore copper connector has mounting holes having a diameter of 3 mm and 4 mm, respectively, while the two mounting holes are perpendicular to one another.

4. The multi-function clamp of claim 1, wherein the connection assembly includes a chamfer head screw, a single-hole copper connector and a hand screw, wherein the chamfer head screw is positioned through the lower clip to secure the lower clip to the single-hole copper connector so as to lock the single-hole copper connector to the lower clip.

5. The multi-function clamp of claim 4, wherein the single-hole copper connector has a mounting hole having a diameter of 4 mm, wherein the mounting hole installs with the lead wires plug and the hand screw is screwed into the single-hole copper connector to secure the lead wires plug within the mounting hole.

6. The multi-function clamp of claim 4, wherein a bottom of the hand screw forms a snap connector.

7. The multi-function clamp of claim 1, characterized in that the foresaid connection assembly includes double-headed electrode socket and a rivet, wherein by coordination of the rivet and the double-headed electrode socket so as to install the double-headed electrode socket on the lower clip.

8. The multi-function clamp of claim 7, wherein the double-headed electrode socket has mounting holes having a diameter of 3 mm and 4 mm respectively, while the bottom of the rivet forms a snap.

9. The multi-function clamp of claim 1, wherein the lower clip has a plurality of teeth, and the connection assembly installs in a foot section of the lower clip.

10. The multi-function clamp of claim 1, wherein a tail end of the upper clip has wavy stripes and the front end has multiple dots, the upper clip having a plurality of teeth positioned to nest with another plurality of teeth on the lower clip.

11. The multi-function clamp of claim 5, wherein a bottom of the hand screw comprises a snap.

* * * * *